(12) United States Patent
Su et al.

(10) Patent No.: US 8,372,585 B2
(45) Date of Patent: Feb. 12, 2013

(54) ELECTRONIC SENSING FOR NUCLEIC ACID SEQUENCING

(75) Inventors: Xing Su, Cupertino, CA (US); David Liu, Fremont, CA (US)

(73) Assignee: Intel Corporation, Santa Clara, CA (US)

( * ) Notice: Subject to any disclaimer, the term of this patent is extended or adjusted under 35 U.S.C. 154(b) by 544 days.

(21) Appl. No.: 11/967,600

(22) Filed: Dec. 31, 2007

(65) Prior Publication Data

US 2009/0170716 A1     Jul. 2, 2009

(51) Int. Cl.
*C12Q 1/68* (2006.01)
(52) U.S. Cl. ........................................ 435/6.1
(58) Field of Classification Search .................. None
See application file for complete search history.

(56) References Cited

U.S. PATENT DOCUMENTS

| 7,488,578 | B2 * | 2/2009 | Gumbrecht et al. | 435/6 |
| 2005/0214759 | A1 * | 9/2005 | Wlassof et al. | 435/6 |
| 2006/0199193 | A1 * | 9/2006 | Koo et al. | 435/6 |

OTHER PUBLICATIONS

Stephen S. W. Yeung et al., "Electrochemical Real-Time Polymerase Chain Reaction", J. Am. Chem. Soc. 2006, vol. 128, No. 41, pp. 13374-13375, S1-S2.
Jürgen Fritz et al., "Electronic detection of DNA by its intrinsic molecular charge", PNAS vol. 99 No. 22, published Oct. 29, 2002, p. 14142-14146.
M. Gabig-Ciminska et al., "Electric chips for rapid detection and quantification of nucleic acids", Biosensors and Bioelectronics 19 (2004), accepted Jun. 30, 2003 pp. 537-546.
Marcin Janicki et al., "Ion sensitive field effect transistor modelling for multidomain simulation purposes", Microelectronics Journal 35 (2004), published Jul. 28, 2004, pp. 831-840.
Jim Kling, "Ultrafast DNA Sequencing", Nature Biotechnology vol. 21 No. 12, published Dec. 2003, pp. 1425-1427.
Marcel A. G. Zevenbergen et al., "Mesoscopic Concentration Fluctuations in a Fluidic Nanocavity Detected by Redox Cycling", Nano Lett., vol. 7, No. 2, 2007, published Dec. 22, 2006, pp. 384-388.
U.S. Appl. No. 12/319,168, filed Dec. 31, 2008.

* cited by examiner

*Primary Examiner* — Christopher M Babic
(74) *Attorney, Agent, or Firm* — Julia A. Hodge

(57) ABSTRACT

Methods for sequencing nucleic acids are presented. Sequencing is accomplished through the detection of a redox active species that is indicative of nucleotide incorporation. In embodiments of the invention, an electrochemical signal indicative of nucleotide incorporation is amplified through cycling before it is detected. Arrays are provided that are capable of massively parallel nucleic acid sequence determination.

13 Claims, 7 Drawing Sheets

| Type | Structure |
|---|---|
| Redoxigenic | Redox—(P(=O)(O⁻)—O)₂—P(=O)(X)—O—[sugar]—B<br>X = O, S<br>Y = H or OH<br>B = A, G, C, T<br>R = allyl or alpha-nitrobenzyl<br>Redox = aminophenyl, hydoxyphenyl, naphthyl |
| Base-modifier | ⁻O—(P(=O)(O⁻)—O)₂—P(=O)(X)—O—[sugar]—B—Redox<br>X = O, S<br>Y = H or OH<br>B = A, G, C, T<br>R = allyl or alpha-nitrobenzyl<br>Redox = ferrocene, anthraquinone, methylene blue |
| Sugar-modifier | ⁻O—(P(=O)(O⁻)—O)₂—P(=O)(X)—O—[sugar]—B; sugar-O-Redox<br>X = O, S<br>Y = H or OH<br>B = A, G, C, T<br>R = allyl or alpha-nitrobenzyl<br>Redox = ferrocene, anthraquinone, methylene blue |

Figure 2

ELECTRONIC SENSING FOR NUCLEIC ACID SEQUENCING

BACKGROUND OF THE INVENTION

1. Field of the Invention

The embodiments of the present invention relate generally to sequencing nucleic acid molecules, and more specifically, to sequencing nucleic acid molecules through the electronic detection of oxidation reduction reactions.

2. Background Information

Genetic information in living organisms is contained in the form of very long nucleic acid molecules such as deoxyribonucleic acid (DNA) and ribonucleic acid (RNA). Naturally occurring DNA and RNA molecules are typically composed of repeating chemical building blocks called nucleotides which are in turn made up of a sugar (deoxyribose or ribose, respectively), phosphoric acid, and one of four bases, adenine (A), cytosine (C), guanine (G), and thymine (T) or uracil (U). The human genome, for example, contains approximately three billion nucleotides of DNA sequence and an estimated 20,000 to 25,000 genes. DNA sequence information can be used to determine multiple characteristics of an individual as well as the presence of and or susceptibility to many common diseases, such as cancer, cystic fibrosis, and sickle cell anemia. Determination of the entire three billion nucleotide sequence of the human genome has provided a foundation for identifying the genetic basis of such diseases. A determination of the sequence of the human genome required years to accomplish. Sequencing the genomes of individuals provides an opportunity to personalize medical treatments. The need for nucleic acid sequence information also exists in research, environmental protection, food safety, biodefense, and clinical applications, such as for example, pathogen detection (the detection of the presence or absence of pathogens or their genetic variants).

Thus, because DNA sequencing is an important technology for applications in bioscience, such as, for example, the analysis of genetic information content for an organism, tools that allow for faster and or more reliable sequence determination are valuable. Applications such as, for example, population-based biodiversity projects, disease detection, personalized medicine, prediction of effectiveness of drugs, and genotyping using single-nucleotide polymorphisms, stimulate the need for simple and robust methods for sequencing short lengths of nucleic acids (such as, for example, those containing 1-20 bases). Sequencing methods that provide increased accuracy and or robustness, decreased need for analysis sample, and or high throughput are valuable analytical and biomedical tools.

BRIEF DESCRIPTION OF THE FIGURES

FIG. 2 shows exemplary schemes for the attachment of a redox active species to a nucleotide.

DETAILED DESCRIPTION OF THE INVENTION

Figure 1:
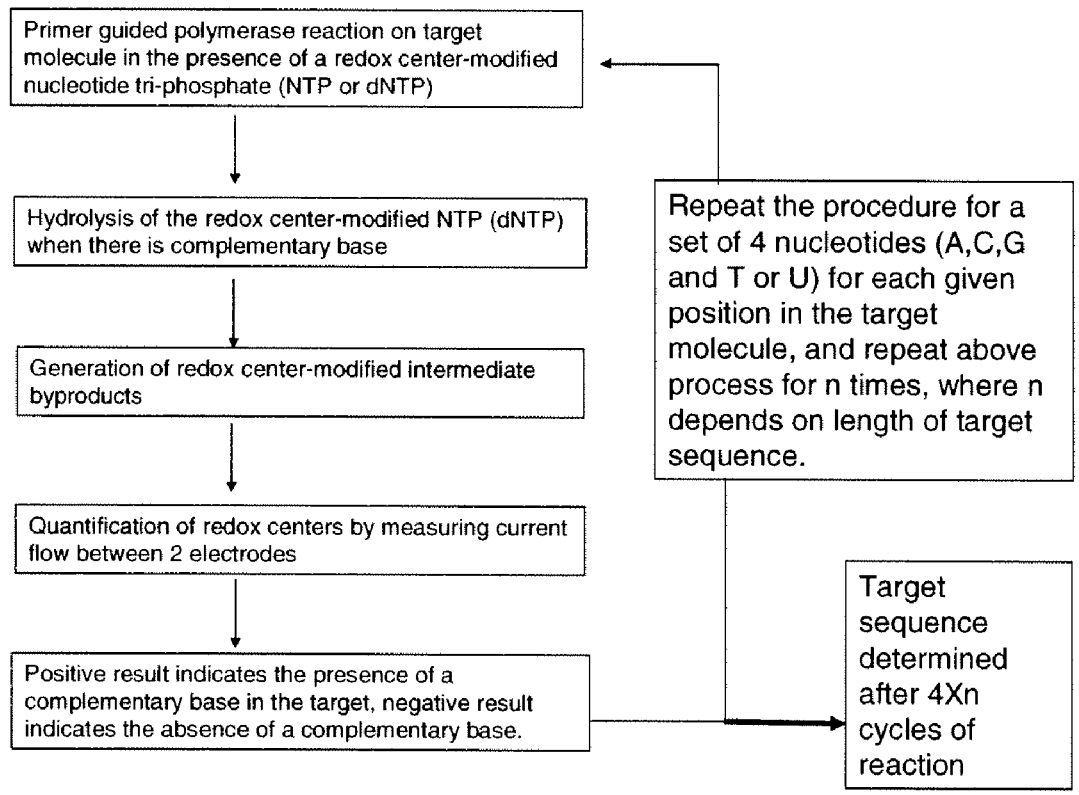
FIG. 1 provides a flow diagram of a method for determining the sequence of a nucleic acid molecule.

Embodiments of the present invention provide devices and methods for sequencing nucleic acids and nucleic acid detection. Methods are provided according to embodiments of the invention by which whole genomes of organisms can be sequenced. In general, the types of nucleic acids that can be sequenced include polymers of deoxyribonucleotides (DNA) or ribonucleotides (RNA) and analogs thereof that are linked together by a phosphodiester bond. A polynucleotide can be a segment of a genome, a gene or a portion thereof, a cDNA, or a synthetic polydeoxyribonucleic acid sequence. A polynucleotide, including an oligonucleotide (for example, a probe or a primer) can contain nucleoside or nucleotide analogs, or a backbone bond other than a phosphodiester bond. In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine, or uracil linked to ribose. However, a polynucleotide or oligonucleotide also can contain nucleotide analogs, including non-naturally occurring synthetic nucleotides or modified naturally occurring nucleotides.

The covalent bond linking the nucleotides of a polynucleotide generally is a phosphodiester bond. However, the covalent bond also can be any of a number of other types of bonds, including a thiodiester bond, a phosphorothioate bond, a peptide-like amide bond or any other bond known to those in the art as useful for linking nucleotides to produce synthetic polynucleotides. The incorporation of non-naturally occurring nucleotide analogs or bonds linking the nucleotides or analogs can be particularly useful where the polynucleotide is to be exposed to an environment that can contain nucleolytic activity, since the modified polynucleotides can be less susceptible to degradation.

Virtually any naturally occurring nucleic acid may be sequenced including, for example, chromosomal, mitochondrial or chloroplast DNA or ribosomal, transfer, heterogeneous nuclear or messenger RNA. RNA can be converted into more stable cDNA through the use of a reverse transcription enzyme (reverse transcriptase). Additionally, non-naturally occurring nucleic acids that are susceptible to enzymatic synthesis and degradation may be used in embodiments of the present invention.

Methods for preparing and isolating various forms of nucleic acids are known. See for example, Berger and Kimmel, eds., *Guide to Molecular Cloning Techniques*, Methods in Enzymology, Academic Press, New York, N.Y. (1987); Sambrook, Fritsch and Maniatis, eds., *Molecular Cloning: A Laboratory Manual*, 2nd Ed., Cold Spring Harbor Press, Cold Spring Harbor, N.Y. (1989); and Ausbel, F. M., et al., eds., *Current Protocols in Molecular Biology*, Wiley and Sons, Inc. (2007). Samples comprising RNA can be converted to DNA for sequencing using a reverse transcriptase enzyme to synthesize a complementary strand of DNA from the RNA molecule. Commercial kits for preparing nucleic acids are available, such as, for example, the SuperScript™ Double-Stranded cDNA Synthesis Kit from Invitrogen.

FIG. 1 provides a general flow diagram describing a method that is useful for sequencing a nucleic acid molecule, SNP (single nucleotide polymorphism) detection, and gene expression. In FIG. 1, a nucleic acid molecule is attached to a surface inside a well. A solution is provided to the well containing a primer complementary to a section of the nucleic acid target. The primer DNA molecule hybridizes to a section of the DNA molecule attached inside the well and primes the attached DNA molecule for synthesis of a complementary strand of DNA. If the sequence of DNA inside the well is unknown, the primer might be one of many having random sequences provided to the DNA strand inside the well. After the primer is allowed to hybridize to the DNA molecule inside the well, a solution containing a DNA polymerase enzyme and a redox-center modified nucleotide triphosphate (NTP or dNTP) is added. The dNTP contains either a reodox modified deoxyadenosine triphosphate (dATP), deoxycytidine triphosphate (dCTP), deoxyguanosine triphosphate (dGTP), deoxythymidine triphosphate (dTTP), or uridine triphosphate (UTP). For example, if a redox-modified dATP has been provided and thymidine is the next complementary nucleic acid in the sequence, then the redox-modified dATP is incorporated into the growing DNA strand. Where there is a cytosine on the strand to be sequenced, a guanine will be incorporated, where there is a thymidine, an adenosine will be incorporated, and vice versa. If dATP is not the next complementary nucleic acid, then no chemistry occurs inside the well. Products of the reaction are then detected. If no reaction has occurred, then the redox-center modified reaction products are not detected. Thus, a positive result (the detection of redox-center modified reaction products) indicates that dATP (in this example) is the next complementary nucleic acid in the growing chain. If a negative result is found, this method is then repeated for the three remaining redox-center modified nucleotides until a positive result is achieved to determine the identity of the complementary base.

The process shown in FIG. 1 can be integrated into a miniaturized device, such as a microfluidic or a nanofluidic device. Additionally, the procedure shown in FIG. 1 can be automated though the use of a computer to control the delivery of reagents and monitor the results from redox potential measurements. Sequence data is assembled from multiple cycles of reactions. Further, the process shown in FIG. 1 can be performed in a highly parallel manner using an array of reaction cavities (or wells) in which a nucleic acid to be sequenced is immobilized. Microscale fluidic devices typically have interior features for fluid flow and containment having diameters of 500 μm or less. A μm is $10^{-6}$ meters. Nanoscale fluidic devices typically have interior features for fluid flow and containment having diameters of 500 nm or less. A nm is $10^{-9}$ meters.

Typically nucleic acid sequencing will be performed on a sample containing long polymers of nucleic acids. The sample is prepared by cutting the long polymers into smaller polymers of 50 nucleotides in length or less. Cutting long DNA polymers is done using a restriction enzyme or through shearing using mechanical forces. The smaller single-stranded nucleic acid polymers are then immobilized in wells. The wells form an array of wells wherein the wells are capable of measuring an electrical potential for the contents of a solution in the well. The concentration of the smaller nucleic acid polymers is controlled so that there is statistically approximately one polymer in solution for each well or the concentration of DNA attachment sites within the wells is controlled so that there is statistically one attachment site for each well. The smaller DNA strands are primed and the method shown in FIG. 1 is then repeated 4N times, where N is the number of bases in the longest DNA molecule being sequenced, in order to determine the sequence of the DNA sample being sequenced.

The immobilized DNA molecules can either be a sample to be sequenced or capture DNA probes of known sequence can be first immobilized and then the sample to be sequenced can be hybridized to the immobilized probes. The capture probes have a sequence designed to hybridize to sections of the sample DNA. Typically, DNA fragments to be immobilized are diluted so that statistically each sensor has one DNA molecule immobilized. Information from electrodes showing ambiguous results is disregarded. Sequence information is assembled from the sensors having a single DNA molecule immobilized.

DNA can be immobilized in the reaction cavity by standard methods, such as for example, through biotin-avidin or antibody-antigen binding. Biotin, avidin, antibodies, or antigens can be attached, for example, to an insulating layer comprised of silicon dioxide through derivatization of the silicon dioxide surface with, for example, (3-aminopropyl)triethoxysilane to yield a surface that presents an amine group for molecule attachment. The molecule can be attached by using water-soluble carbodiimide coupling reagents, such as EDC (1-ethyl-3-(3-dimethyl aminopropyl)carbodiimide), which couples carboxylic acid functional groups with amine groups. DNA molecules bearing a corresponding coupling agent can then be attached through the surface through, for example, a biotin-avidin or antibody-antigen interaction. Additionally, acrydite-modified DNA fragments can be attached to a surface modified with thiol groups and amine-modified DNA fragments can be attached to epoxy or aldehyde modified surfaces. The density of attached DNA molecules is controlled by providing blocking groups, i.e., groups that are not able to attach or bind a molecule along with the molecules that bind other molecules, such as for example, bovine serum albumen protein or non-functional silane molecules (molecules capable of silanating a silicon dioxide surface, but that do not present a functional group for further molecular attachment), on the surface for DNA attachment. By controlling the concentration of blocking and non-blocking molecules in the solution used to coat the surface for DNA binding, a statistically one DNA molecule is bound in the cavity for electrochemical detection. If the DNA is bound to the surface through a biotin-avidin interaction, the biotin-labeled DNA can be presented to the surface for attachment in a solution that also contains free biotin in a concentration to statistically end up with one DNA molecule in a cavity.

FIG. 2 provides exemplary nucleosides having redox active species attached. A redoxigenic nucleotide has a redox active species attached to the γ-phosphate group of the nucleoside base. As shown in FIG. 2, the base for the redoxigenic nucleotide may be an A, G, C, or T. Redox active species include, for example, an aminophenyl, a hydroxyphenyl, and napthyl groups. A redox active species may also be attached to the nucleotide base. The base may be an A, G, C, or T and the redox active species may be, for example a ferrocene, an anthraquinone, or a methylene blue molecule. A third redox active group attachment motif includes one in which the redox active group is attached to the sugar group of the nucleotide base. For the sugar-attached redox-modified nucleotide, the base may be an A, G, C, or T and the redox active species may be, for example a ferrocene, an anthraquinone, or a methylene blue molecule.

In general, a redox active species is a molecule that is capable of cycling through states of oxidation and or reduction without decomposing or reacting irreversibly with other molecules in solution. A redox reaction is a reaction in which both oxidation and reduction is occurring.

Typical useful polymerase enzymes include DNA polymerases with or without 3' to 5' exonuclease activities, such as for example, E. coli DNA polymerase I, Klenow fragment of E. Coli DNA polymerase I, Therminator DNA polymerase, reverse transcriptase, Taq DNA polymerase, Vent DNA polymerase (all available from New England Biolabs, Inc., Beverly, Mass.), T4 DNA polymerase, and Sequenase (both available from USB, Cleveland, Ohio).

Figure 3:
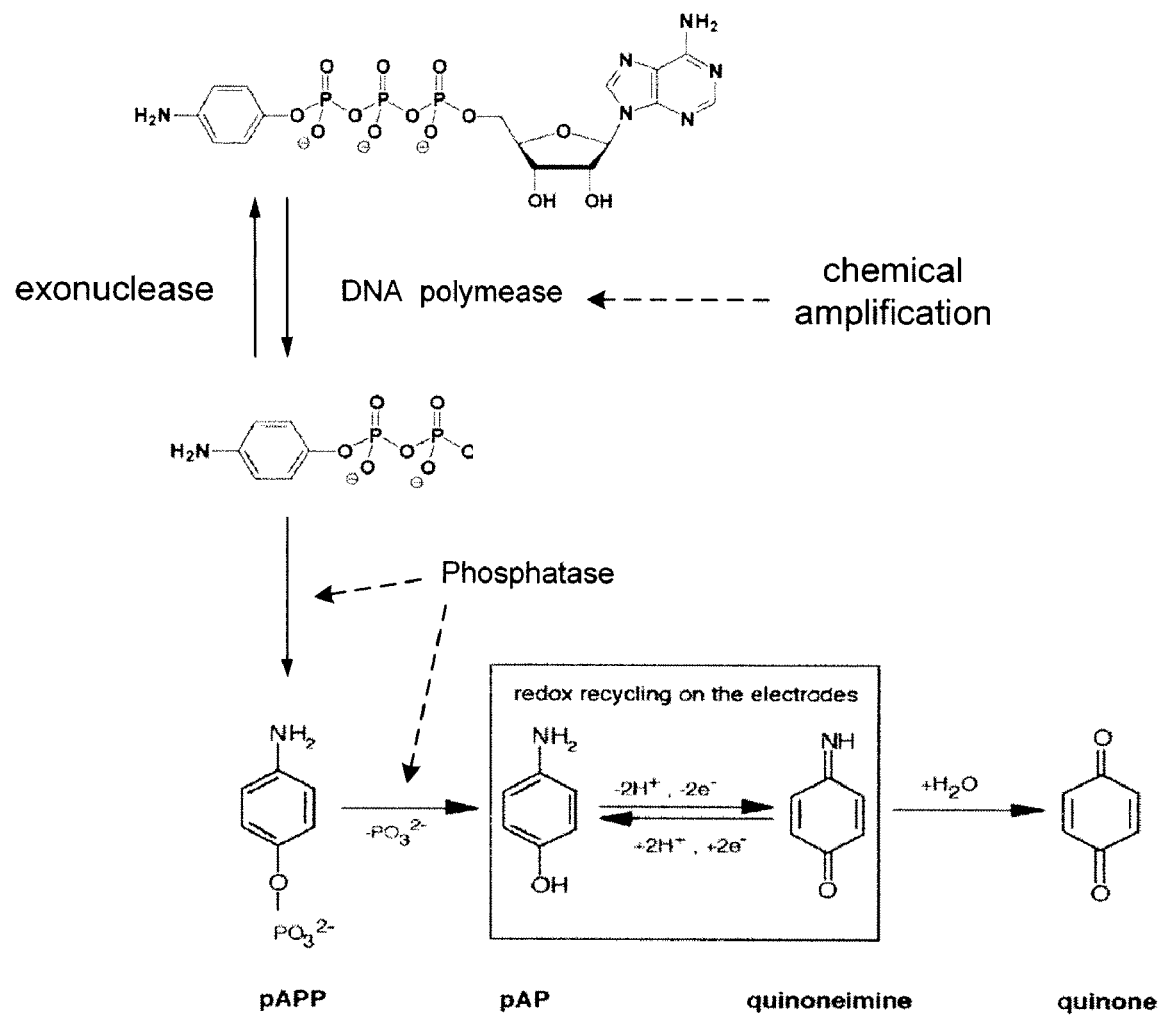
FIG. 3 provides a reaction scheme showing a method for sequencing a nucleic acid molecule through the detection of an oxidation-reduction reaction of a redox active species cleaved from a nucleoside-associated pyrophosphate group.

FIG. 3 illustrates a method for sequencing a DNA molecule through chemically amplifying the redox signal obtained when a nucleotide base is complementary to the base provided by the template strand being sequenced. The method of FIG. 3 provides for chemical amplification of the signal when a complementary base in incorporated into a growing complementary strand. The primed growing DNA molecule is terminated with a nuclease resistant base through the action of a polymerase enzyme. In this example, the redox labeled NTP is γ-aminophenyl-adenine-triphosphate (dATP). The incorporation of a complementary redox labeled nucleotide into the growing strand releases the redox labeled pyrophosphate (PPi) group into solution. The action of a phosphatase enzyme removes the pyrophosphate from the redox molecule. Useful phosphatase enzymes include alkaline phosphatase, acid phosphatase, protein phosphatase, polyphosphate phosphatase, sugar-phosphatase, and pyrophosphatase. In this example, the redox active species is the p-aminopheonol (pAP) and quinoneimine pair. The number of p-aminopheonol molecules released into solution is amplified through the cycling of the incorporation excision reactions. Specifically, a complementary nucleotide is incorporated, an exonuclease enzyme removes the incorporated complementary nucleotide, and then DNA polymerase incorporates a second complementary nucleotide and a second redox labeled pyrophosphate group is released into solution. Through these repeated cycles of incorporation and removal, the concentration of the redox active species builds up in solution. In this way, the signal resulting from the incorporation of a complementary base into the growing complementary strand is amplified. The presence of the redox active species free of phosphate groups is detected electrochemically. Optionally, the redox active species are recycled between two electrodes to amplify the signal further. As described more fully herein, the signal amplification technique of cycling redox active species between electrodes is referred to as redox cycling. By moving between electrodes, each redox active species contributes multiple electrons to the measured current, thereby amplifying the measured current. If the nucleotide supplied to the reaction is not complementary to the growing DNA strand, then the free redox active species is not detected. Once a nucleotide incorporation has been detected, the growing strand is provided with a nuclease-resistant base that is complementary to the next space in the template DNA molecule that is being sequenced.

A variety of polymerases are available that can incorporate ribonucleotides or modified nucleotides into DNA, such as for example, the commercially available Therminator DNA polymerase (available from New England Biolabs, Inc., Beverly, Mass.) or genetically engineered DNA polymerase. See also, for example, DeLucia, A. M., Grindley, N. D. F., Joyce, C. M., *Nucleic Acids Research*, 31:14, 4129-4137 (2003); and Gao, G., Orlova, M., Georgiadis, M. M., Hendrickson, W. A., Goff, S. P., *Proceedings of the National Academy of Sciences*, 94, 407-411 (1997). Nuclease-resistant nucleotides can be ribonucleotides or other modified nucleotides. Exemplary nuclease resistant bases that can be incorporated into growing DNA strands but that are resistant to digestion by exonucleases (such as the 3' to 5' exonuclease active DNA polymerases or exonuclease I and III) include alpha phosphorothioate nucleotides (available from Trilink Biotechnologies, Inc., San Diego, Calif.). Additionally, ribonucleotides can be incorporated into a growing DNA strand by Therminator DNA polymerase or other genetically engineered or mutated polymerases, but the ribonucleotide bases are resistant to digestion by exonucleases, such as exonucleases I or exonuclease III (available from New England Biolabs). Exemplary nucleases that cannot digest these resistant bases include exonuclease I, nuclease III, and 3' to 5' exonuclease active DNA polymerases.

Figure 4:
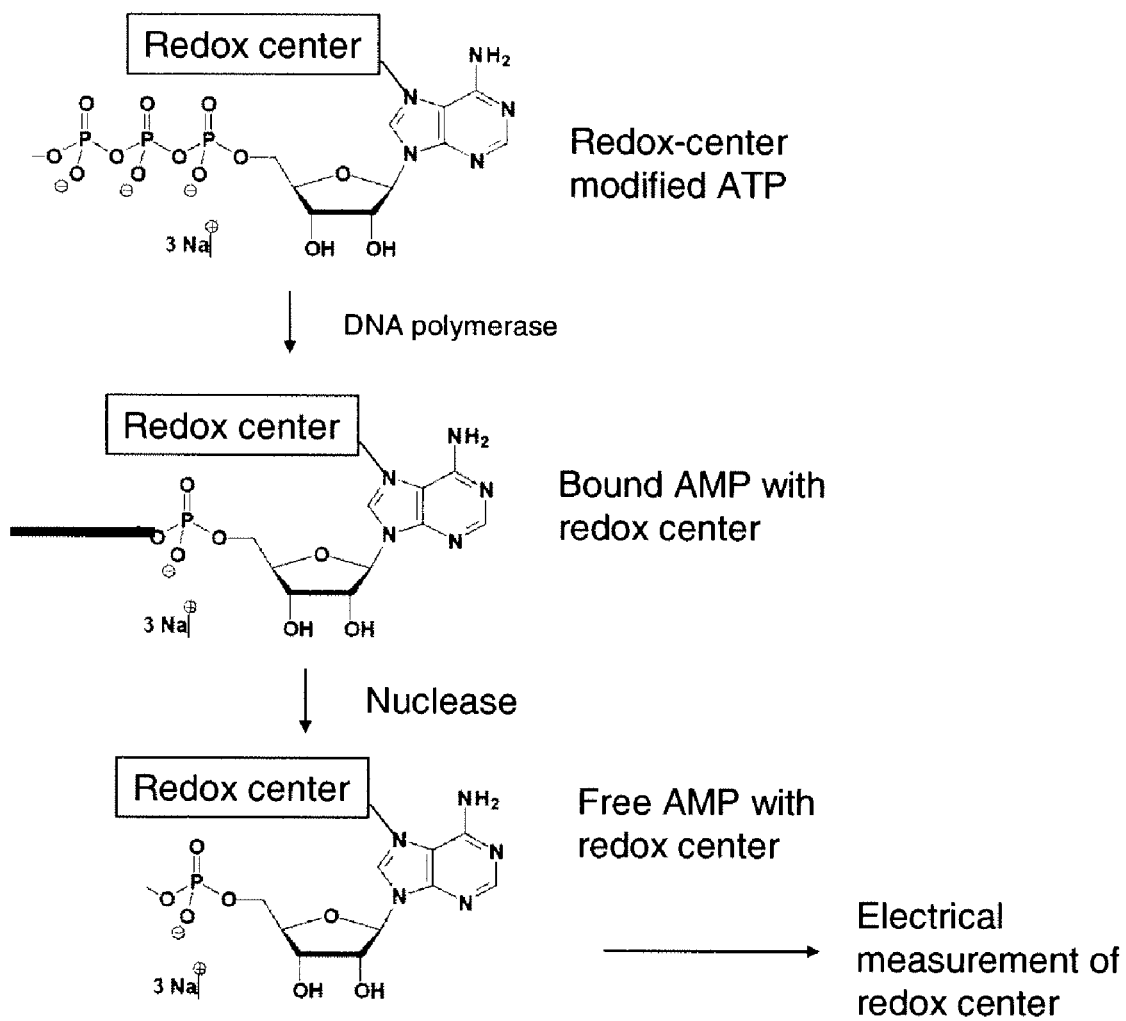
FIG. 4 provides a reaction scheme showing a method for sequencing a nucleic acid molecule through the detection of an oxidation-reduction reaction of a redox active species bound to a nucleotide base.

FIG. 4 provides an exemplary method for sequencing a nucleic acid molecule using an electrochemically detectable reaction. In the example presented in FIG. 4, a redox active species is attached to the adenine of a dATP molecule. A single nucleic acid molecule to be sequenced (not shown) is attached to a surface inside an electrode cavity. The nucleic acid is primed and the growing complementary strand (shown as a dark line) is terminated with a nuclease resistant nucleotide. The redox-modified dATP molecule is incorporated into the growing complementary strand through the action of a DNA polymerase enzyme present in the solution in the electrode cavity. The excess redox-modified ATP from the polymerase reaction is washed away from the reaction site. The redox-modified dAMP is then excised from the growing complementary DNA strand through the action of a nuclease enzyme present in the solution in the electrode cavity. The redox-modified dAMP is detected electrochemically through redox cycling. If dATP is not the next complementary nucleic acid, no redox signal is detected after the reaction solution is washed from the electrode cavity. This method is then repeated for the three other nucleotides. Once the next complementary nucleotide has been determined, the growing complementary nucleic acid strand is terminated with a complementary redox resistant base and the next complementary base is determined.

In alternate embodiments, the method shown in FIG. 4, more than one copy of the nucleic acid molecule to be sequenced is attached in the electrode cavity. The attachment of a plurality of copies of the nucleic acid to be sequenced amplifies the signal detected when a complementary nucleotide triphosphate is provided to the cavity. Theoretically, providing 100 nucleotides to the cavity amplifies the signal about 100 times, although the actual result is most often slightly lower. The detected signal can then optionally be amplified further through redox cycling techniques.

Figure 5:
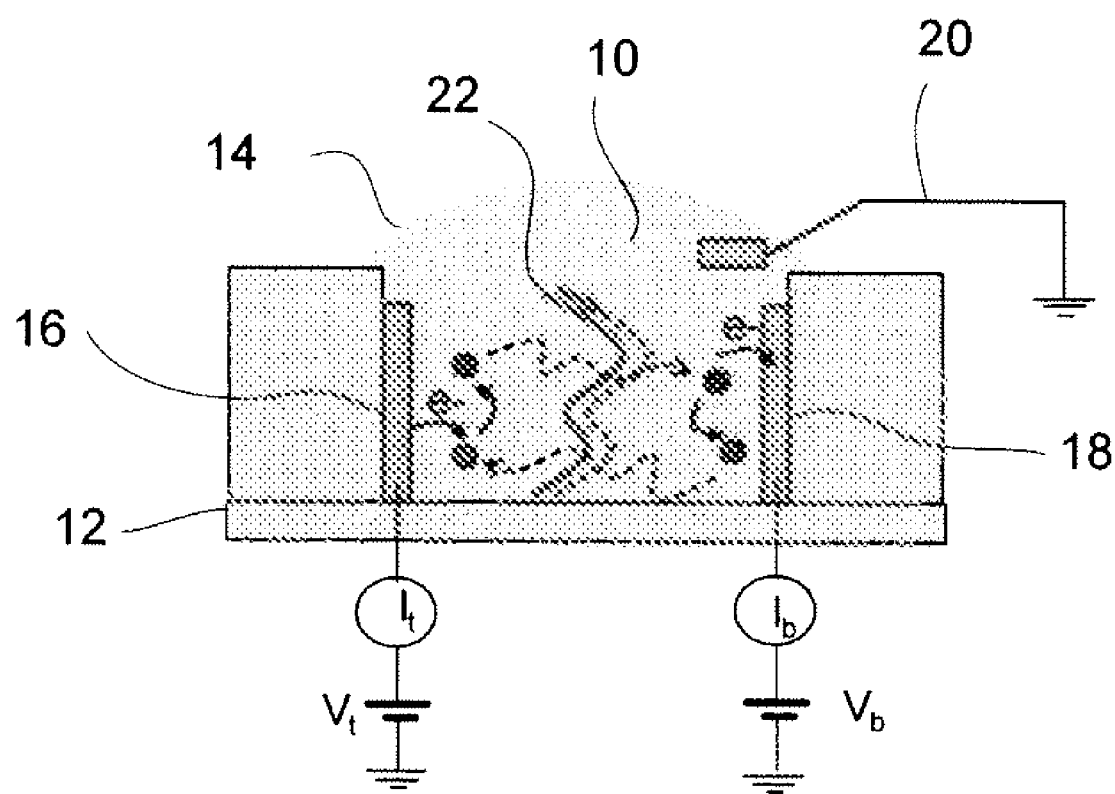
FIG. 5 shows an exemplary device for sequencing a nucleic acid through the electrochemical detection of a redox active species.

FIG. 5 provides a drawing of an electrochemical device in which nucleic acids can be sequenced through the detection of an electroactive species using redox cycling for signal amplification. In FIG. 5, a cavity 10 in a substrate 12 capable of containing a fluid 14 is provided with at least two electrodes 16 and 18. The electrodes 16 and 18 are comprised of electroactive materials, such as, for example, carbon, nickel, tungsten, aluminum, platinum, palladium, indium tin oxide, or gold. A reference electrode 20 placed in the bulk solution provides a standard by which to compare the measured voltage in the cavity. A reference electrode provides a redox reaction having a known value to which the value measured for the redox reaction in the cavity can be referenced. An anode is the electrode at which oxidation of molecules in solution occurs and the cathode is the electrode where reduction occurs. As described more fully herein, cavity dimensions are on the nanometer scale and the separation between the electrodes in the cavity is of the order of 500 nm or less, for signal amplification techniques. A nucleic acid molecule to be sequenced 22 is immobilized in the reaction cavity 10. The cavity 10 is provided with a solution containing a redox-modified nucleic acid and a nucleic acid polymerase enzyme. Incorporation of a NMP into the complementary DNA strand 24 is detected through the detection of a redox species indicative of the products of the incorporation reaction. More specifically, a current flow is detected at a voltage indicative of the oxidation/reduction reaction specific to a product of the incorporation reaction. In FIG. 5, Vt and Vb are the potentials applied to the left and right electrodes with respect to a reference electrode immersed in the bulk reservoir. The values It and Ib are the values measured for the corresponding currents. A current flow is detected at the redox potential for a redox active species present in the solution.

Optionally, the current flow/voltage signal that is measured from the cavity is amplified by redox cycling. Redox cycling is a technique in which multiple electrodes are used to repeatedly flip the charge state of the redox active molecules allowing each redox active molecule to participate in multiple redox reactions and thereby contribute multiple electrons to the measured current value. An exemplary redox cycling technique is described in, "Mesoscopic Concentration Fluctuation in a Fluidic Nanocavity Detected by Redox Cycling," Zevenbergen, M. A., Krapf, D., Zuiddam, M. R., Lemay, S. G., *Nano Letters,* 7:384 (2007) (and references therein). Redox cycling is a technique that is also used in scanning electrochemical microscopy. In this technique, two closely spaced planar electrodes are provided and the product of a reversible redox reaction at one electrode serves as a reactant at the other electrode and vice versa. The space between the electrodes is on the nanometer scale. Redox-active molecules diffuse in the cavity between the two electrodes shuttle multiple electrons between the electrodes, leading to amplification of the measured electrochemical current. Signals from the redox active species are amplified greater than 100 times.

Nucleic acid sequencing is performed in a massively parallel manner using arrays of reaction cavities. A sample comprising nucleic acid molecules is presented to the array in a manner that results in statistically one nucleic acid molecule per reaction cavity. Reactions as described in FIG. 1 are run in the cavities of the array. Electronics coupled to the reaction cavities detect the incorporation of nucleic acids in the cavities. Data from cavities that is inconsistent is discarded. Sequence information for each nucleic acid in a cavity is built through multiple reaction cycles.

Array compositions may include at least a surface with a plurality of discrete reaction cavities (indentations or wells). The size of the array will depend on the end use of the array. Arrays containing from about two to many millions of different discrete reaction cavities can be made. Generally, the array size will depend in part on the size of the surface from which the array is made. Very high density, high density, moderate density, low density, or very low density arrays can be made. Some ranges for very high-density arrays are from about 100,000,000 to about 1,000,000,000 cavities per array. High-density arrays range from about 1,000,000 to about 100,000,000 cavities. Moderate density arrays range from about 10,000 to about 100,000 cavities. Low-density arrays are generally less than 10,000 cavities. Very low-density arrays are less than 1,000 cavities.

The reaction cavities can comprise a pattern or a regular design or configuration or can be randomly distributed. A regular pattern of cavities can be used such that the cavities can be addressed in an X-Y coordinate plane. The surfaces within the cavities can be modified to allow attachment of analytes in individual cavities. In general, reaction cavities are a depression or well in the surface of the substrate that is capable of containing a liquid.

There are numerous suitable methods for patterning an array of nanoscale features on a surface of a substrate. Examples of such suitable methods include lithography methods such as, for example, interferometric lithography (IL), immersion interferometric lithography, electron beam lithography, scanning probe lithography, nanoimprint, extreme ultraviolet lithography, and X-ray lithography, and stamping, etching, microetching, and molding techniques. The technique used will depend in part on the composition and shape of the substrate. Generally, lithography is a highly specialized printing process used to create detailed patterns on a substrate, such as a silicon wafer. An image containing a desired pattern is projected onto the wafer, which is coated by a thin layer of photosensitive material called resist. The bright parts of the image pattern cause chemical reactions which, in turn, render the resist material soluble, and, thus, dissolve away in a developer liquid, whereas the dark portions of the image remain insoluble. After development, the resist forms a stenciled pattern across the wafer surface, which accurately matches the desired pattern. Finally, the pattern is permanently transferred into the wafer surface, for example by a chemical etchant, which etches (removes) those parts of the surface unprotected by the resist.

In various embodiments of the invention, arrays may be incorporated into a larger apparatus and/or system. In certain embodiments, the substrate may be incorporated into a micro-electro-mechanical system (MEMS). MEMS are integrated systems comprising mechanical elements, sensors, actuators, and electronics. All of those components may be manufactured by known microfabrication techniques on a common chip, comprising a silicon-based or equivalent substrate (See for example, Voldman et al., *Ann. Rev. Biomed. Eng.,* 1:401-425 (1999).) The sensor components of MEMS may be used to measure mechanical, thermal, biological, chemical, optical and/or magnetic phenomena. The electronics may process the information from the sensors and control actuator components such as pumps, valves, heaters, coolers, and filters, thereby controlling the function of the MEMS.

In some embodiments of the invention, substrates may be connected to various fluid filled compartments, such as microfluidic channels, nanochannels, and or microchannels. These and other components of the apparatus may be formed as a single unit, for example in the form of a chip, such as semiconductor chips and or microcapillary or microfluidic chips. Alternatively, the substrates may be removed from a silicon wafer and attached to other components of an apparatus. Any materials known for use in such chips may be used in the disclosed apparatus, including silicon, silicon dioxide, silicon nitride, polydimethyl siloxane (PDMS), polymethylmethacrylate (PMMA), plastic, glass, and quartz.

Techniques for batch fabrication of chips are well known in the fields of computer chip manufacture and or microcapillary chip manufacture. Such chips may be manufactured by any method known in the art, such as by photolithography and etching, laser ablation, injection molding, casting, molecular beam epitaxy, dip-pen nanolithography, chemical vapor deposition (CVD) fabrication, electron beam or focused ion beam technology or imprinting techniques. Non-limiting examples include conventional molding with a flowable, optically clear material such as plastic or glass; photolithography and dry etching of silicon dioxide; electron beam lithography using polymethylmethacrylate resist to pattern an aluminum mask on a silicon dioxide substrate, followed by reactive ion etching. Methods for manufacture of nanoelectromechanical systems may be used for certain embodiments of the invention. See for example, Craighead, *Science,* 290:1532-36, (2000). Various forms of microfabricated chips are commercially available from, for example, Caliper Technologies Inc. (Mountain View, Calif.) and ACLARA BioSciences Inc. (Mountain View, Calif.).

Figure 6:
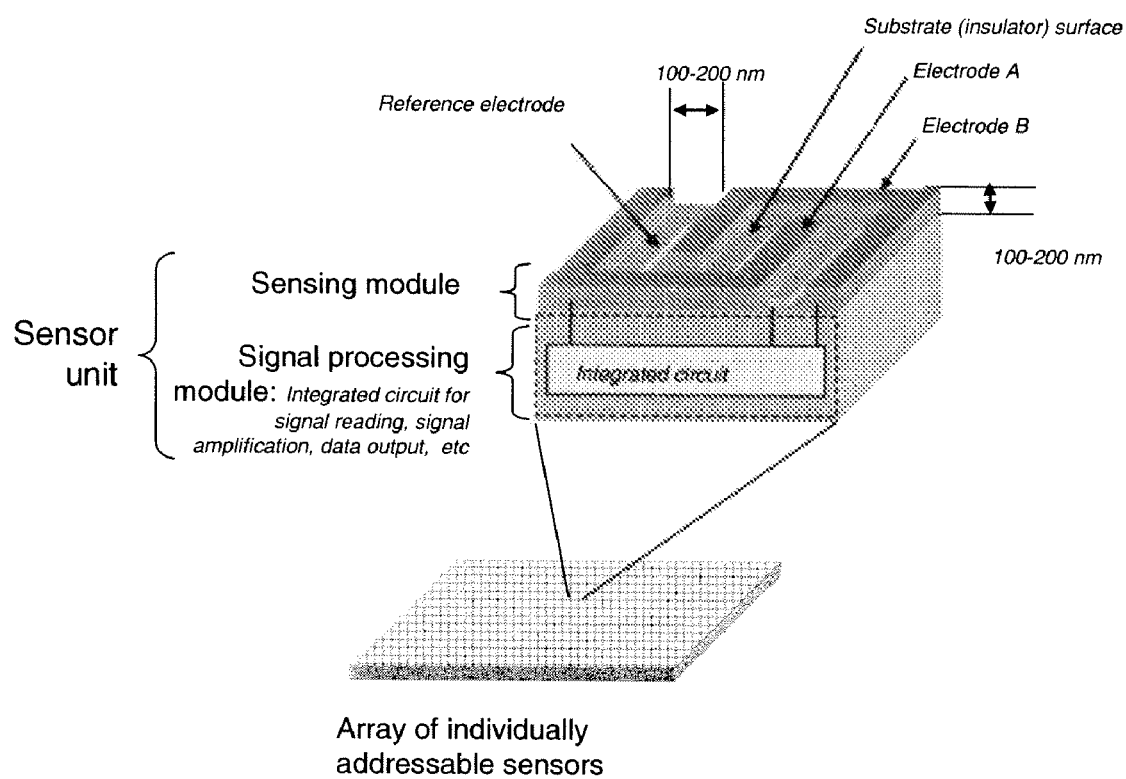
FIG. 6 shows and exemplary electrode cavity for performing sequencing reactions in which redox cycling can be performed.

In an exemplary embodiment, an array of individually addressable sensors is made using standard CMOS processes. Each sensor has two functional modules: the sensing module and the signal processing module. As shown in FIG. 6, the sensing module is built on top of the signal processing module and has three electrodes: one reference electrode and two sensing electrodes. The electrodes are made up of gold or platinum metal. The reference electrode is placed between the sensing electrodes. The gap between the sensing electrodes is 100 to 200 nm. The thickness of the sensing electrodes is also 100 to 200 nm. Therefore, there is a nano-gap between the two sensing electrodes. The signal processing module has integrated circuits that control the potentials of each sensing electrode relative to the reference electrode. The circuits also measure currents associated with the electrodes. The current signals are background-subtracted, amplified, and finally output. The number of sensors in an array are chosen based on the complexity of a DNA sample, assuming 10-30% of the sensors are effective and a 10× redundancy for a 50 base read length. For example, about 5 million (5M) sensors are needed in an array to sequence the *E. coli* genome with a 10× redundancy. If each sensor occupies a space of 10 microns×10 microns (the actual area devoted to sensing (the sensing cavity) is much smaller), the sensor array chip will have a size of 2.5 cm×2.5 cm.

A silicon-oxide surface or insulator region is provided within the sensing module (cavity). This silicon-oxide surface is coated with poly dA adaptor through a 5' silane group attached to the 5' end of the poly dA molecule. Each sensing module is provided with multiple poly dA adaptors. DNA molecules from a bacterium colony are purified and fragmented enzymatically or mechanically to an average size of 150 base pairs long (about 50 nm long). The double-stranded DNA fragments are tailed with poly dT using terminal transferase enzyme and following standard procedures. The poly dT tailed DNA fragments are denatured by heat and hybridized to the poly dA adaptor through the poly dT tail. The amount of DNA that is applied to the sensor array is adjusted so that on average one sensor cavity has one single-stranded DNA fragment (sequencing target molecule) attached to the silicon-oxide surface within the sensing region. Considering the relative dimensions of the DNA molecules and the electrodes, the DNA target molecules are located in the electrode nano-gaps.

Figure 7:
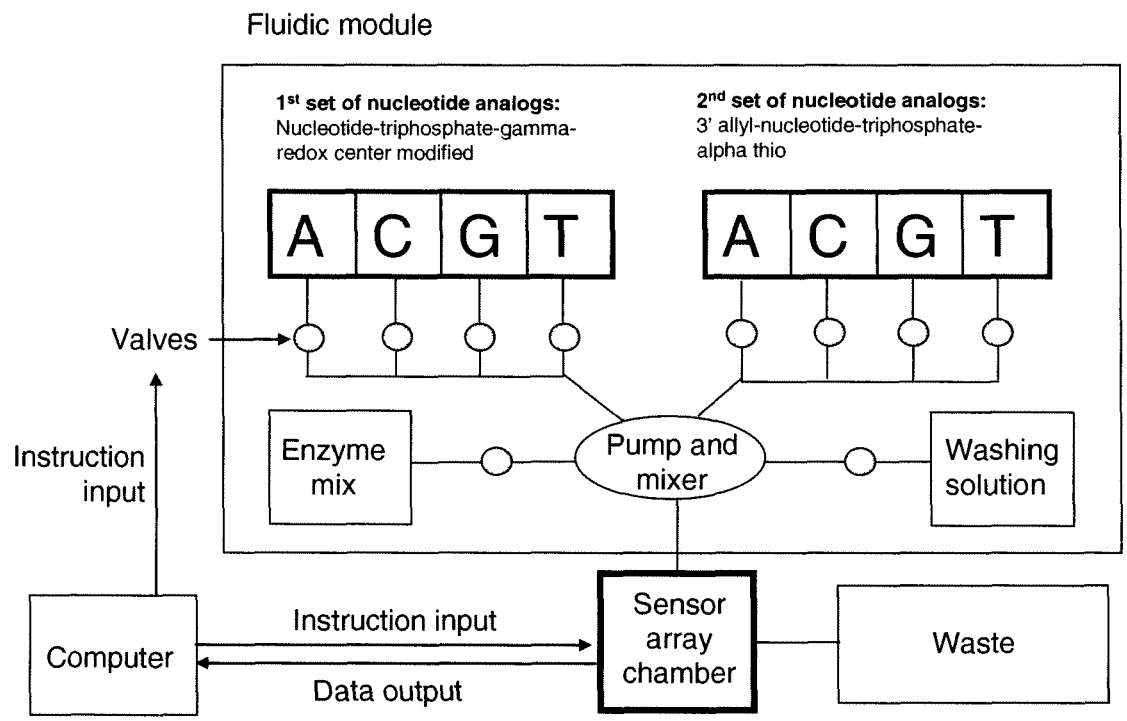
FIG. 7 diagrams a system for performing a sequencing reaction using an array of sensors.

Bacterial strains and potential drug-resistant mutations are identified by whole genome sequencing using a single sensor array chip. The 5M sensor array is placed in a fluidic chamber connected to a set of reservoirs containing each containing one of the four nucleotides; each of the four nucleotide molecules is modified at the γ-phosphate with an amine phenol group. A diagram of an exemplary fluidic array s provided in FIG. 7. The fluidic chamber is also connected to a reservoir of an enzyme solution containing DNA polymerase and exonuclease, and to a second set of reservoirs containing modified nucleotides that are resistant to exonuclease. The nuclease resistant nucleotides are alpha thiol modificatied and 3' allyl modificatied. The 3' allyl modification is a reversible DNA synthesis terminator. Delivery of reagents to the fluidic chamber is controlled by a pump. To start the sequencing process, the last 3' end base in the anchor poly dA is converted to a nuclease resistant base using a reaction with the second set of modified nucleotides and a polymerase enzyme. After removal of the 3' terminator group, the 4 nucleotides from the first set of redox-center-modified nucleotides are delivered separately and sequentially to the reaction cavity of the chip.

The target molecules to be sequenced attached to the sensors can be grouped into four groups based on the next base in the complementary sequence being synthesized: A, C, G, and T. The A group contains all the molecules that have an A at the n position adjacent to the 3' anchor. When modified T nucleotides are delivered to the chip, the molecules in the A group will produce an amplified signal, because, multiple T molecules (dATP) are hydrolyzed and multiple redox-active centers are released (in a first signal amplification process). The redox group is separated from the redox labeled pyrophosphate (PPi) group released into solution through the action of alkaline phosphatase enzyme that removes the pyrophosphate from the redox molecule. In a second amplification process, redox cycling is occurring at the electrodes and the released redox centers are undergoing multiple oxidation cycles to generate an amplified signal. Through the two amplifications, a base match in a single molecule is identified electronically. Addresses in the sensor array are recorded for molecules having a complementary base A in the next position. The molecules in the remaining three groups are sequenced for the n position. The n position s then filled by a nuclease resistant base and 3' blocked (reversibly terminator) nucleotides (second set). After removal of the reversible terminator from the 3' ends, a new cycle of sequencing reactions for the n+1 position is started. The reactions are repeated until about 50-60 positions for each molecule are sequenced.

Data from the sensors is analyzed as follows. If a sensor has more than one DNA molecule attached within its cavity, there will be more than one possible reading from at least one of the sequenced positions. Therefore, only data from those sensors having one molecule attached in the sensor cavity (an effective sensor) are used in the sequence analysis. Sequences of effective sensors are aligned by computer program. The sequence information can be used as de novo sequencing information or reference sequencing information. Further analysis is performed depending on the quality of the data and purpose of the sequencing task.

We claim:

1. A method for analyzing a nucleic acid comprising:
providing a nucleic acid molecule to be sequenced,
terminating a complementary nucleic acid polymer hybridized to the nucleic acid molecule to be sequenced with a nuclease resistant nucleotide,
providing a solution comprising a polymerase enzyme, an exonuclease enzyme, and a nucleotide comprising a redox group attached to a phosphate group of the nucleotide, under conditions that allow a complementary nucleotide comprising a redox group to be incorporated into the growing complementary polymer by the polymerase enzyme and excised from the growing complementary strand by the exonuclease enzyme a plurality of times thereby creating a plurality of phosphorylated redox molecules,
removing phosphate groups from the phosphorylated redox molecules that are the product of nucleotide incorporation wherein detachment from the nucleotide and removal of the phosphate group causes the redox molecules to become redox active; and
detecting the presence of de-phosphorylated redox molecules that are a product of the incorporation of a nucleotide triphosphate comprising a redox group into the complementary polymer, wherein detection occurs through the detection of an oxidation or reduction potential for the activated redox molecule.

2. The method of claim 1 wherein the redox group is selected from the group consisting of an aminophenyl, a hydroxyphenyl, and a napthyl.

3. The method of claim 1 wherein the solution comprising a polymerase enzyme, an exonuclease enzyme, and a nucleotide comprising a redox group, also comprises a phosphatase enzyme that is capable of removing phosphate groups from a phosphorylated redox molecule.

4. The method of claim 1 wherein the activated redox molecules are detected through the use of redox cycling.

5. The method of claim 1 wherein the terminating, providing, removing, and detecting are performed a plurality of times and sequence information is determined for a section of the nucleic acid molecule to be sequenced comprising a plurality of bases.

6. A method comprising:
   providing an array comprised of a plurality of cavities capable of holding a solution, the plurality of cavities having a surface capable of attaching a DNA molecule and at least two electrodes,
   attaching DNA to the surfaces of the cavities so that statistically one DNA molecule is attached in one cavity,
   terminating a primer strand of DNA hybridized to the DNA to be sequenced with a nuclease-resistant nucleotide,
   providing reactants to the cavities comprising a nucleotide comprising a redox group attached to a terminal phosphate group of the nucleotide, an enzyme capable of extending a DNA molecule, and an enzyme capable of deconstructing a DNA molecule under conditions that allow DNA to be synthesized and deconstructed a plurality of times thereby creating a plurality of phosphorylated redox molecules,
   removing phosphate groups from the redox molecules wherein detachment from the nucleotide and removal of the phosphate group causes the redox molecules to become redox active; and
   detecting the presence of de-phosphorylated redox molecules that are a product of the incorporation and excision of a nucleotide comprising a redox group into the complementary polymer, wherein detection occurs through the detection of an oxidation or reduction potential for the activated redox molecule.

7. The method of claim 6 wherein the array is comprised of 100 to 10,000 cavities.

8. The method of claim 6 wherein the array is comprised of 10,000 to 1,000,000,000 cavities.

9. The method of claim 6 wherein the enzyme capable of extending a DNA molecule is a polymerase enzyme.

10. The method of claim 6 wherein the enzyme capable of deconstructing a DNA molecule is an exonuclease enzyme.

11. The method of claim 6 wherein the redox group is selected from the group consisting of an aminophenyl, a hydroxyphenyl, and a napthyl.

12. The method of claim 6 wherein the solution comprising a polymerase enzyme, an exonuclease enzyme, and a nucleotide comprising a redox group, also comprises a phosphatase enzyme that is capable of removing phosphate groups from a phosphorylated redox molecule.

13. The method of claim 6 wherein the activated redox molecule is detected through the use of redox cycling.

* * * * *